United States Patent
Te Stroet et al.

(10) Patent No.: US 10,619,458 B2
(45) Date of Patent: Apr. 14, 2020

(54) COMPUTER SUPPORTED EXPLORATION AND PRODUCTION OF HETEROGENEOUS DISTRIBUTED HYDROCARBON SOURCES IN SUBSURFACE FORMATIONS BASED ON MICROBIAL PROSPECTING

(71) Applicant: BIODENTIFY B.V., Delft (NL)

(72) Inventors: Christianus Bernardus Maria Te Stroet, Hilversum (NL); Roy Christiaan Montijn, Amsterdam (NL); Evgeni Levin, Delfgauw (NL); Frank Henri Johan Schuren, Veenendaal (NL)

(73) Assignee: BIODENTIFY B.V., Delft (NL)

( * ) Notice: Subject to any disclaimer, the term of this patent is extended or adjusted under 35 U.S.C. 154(b) by 51 days.

(21) Appl. No.: 15/549,067

(22) PCT Filed: Feb. 9, 2016

(86) PCT No.: PCT/NL2016/050093
§ 371 (c)(1),
(2) Date: Aug. 4, 2017

(87) PCT Pub. No.: WO2016/130001
PCT Pub. Date: Aug. 18, 2016

(65) Prior Publication Data
US 2018/0023371 A1    Jan. 25, 2018

(30) Foreign Application Priority Data
Feb. 12, 2015  (NL) .................................... 2014286

(51) Int. Cl.
*C12Q 1/64* (2006.01)
*E21B 41/00* (2006.01)
(Continued)

(52) U.S. Cl.
CPC ............ *E21B 41/0092* (2013.01); *C12Q 1/64* (2013.01); *E21B 49/02* (2013.01); *G06F 16/29* (2019.01);
(Continued)

(58) Field of Classification Search
CPC ............................. E21B 41/0092; C12Q 1/64
(Continued)

(56) References Cited

U.S. PATENT DOCUMENTS 3,033,761 A * 5/1962 Brown .................. G01V 9/007
                                              435/250
9,771,795 B2   9/2017 Knight et al.
(Continued)

FOREIGN PATENT DOCUMENTS

WO        90/02816 A1    3/1990
WO     2014/158132 A1   10/2014
(Continued)

OTHER PUBLICATIONS

International Search Report for International Application No. PCT/NL2016/050093 filed on Feb. 9, 2016 in the name of Biodentify B.V, dated Jun. 6, 2016. 4 pages.
(Continued)

*Primary Examiner* — Taras P Bemko
(74) *Attorney, Agent, or Firm* — Steinfl + Bruno, LLP

(57) ABSTRACT

A computer supported method, computer system and computer program product for exploring and producing a subsurface heterogeneous hydrocarbon source and generating a predictive production map of an area under investigation, based on microbial prospecting. Microbial data representative of microbial activity attributable to hydrocarbon microseepage and hydrocarbon productivity data of a plurality of geographic locations are retrieved and correlated by the computer in a data correlation algorithm, providing a thresh-
(Continued)

old hydrocarbon productivity quantity and a truncated set of the retrieved microbial data. The set identifies individual types of the microorganisms and corresponding individual weighting factors computed by the data correlation algorithm, for distinguishing prospective hydrocarbon productivity quantities from non-prospective hydrocarbon productivity quantities. An estimated subsurface hydrocarbon productivity quantity for a geographical location of the area under investigation is provided by count weighting retrieved microbial data of this location for microorganisms identified in the truncated set, applying the individual weighting factors.

27 Claims, 3 Drawing Sheets

(51) Int. Cl.
G06F 16/29 (2019.01)
G06F 16/951 (2019.01)
E21B 49/02 (2006.01)
E21B 43/26 (2006.01)

(52) U.S. Cl.
CPC ............ *G06F 16/951* (2019.01); *E21B 43/26* (2013.01); *G06F 2216/03* (2013.01)

(58) Field of Classification Search
USPC .................................................. 166/250.16
See application file for complete search history.

(56) References Cited

U.S. PATENT DOCUMENTS

| | | |
|---|---|---|
| 2015/0006083 A1 | 1/2015 | McAuliffe et al. |
| 2015/0284810 A1 | 10/2015 | Knight et al. |
| 2015/0284811 A1 | 10/2015 | Knight et al. |
| 2016/0028365 A1 | 1/2016 | Takeuchi |
| 2017/0139078 A1 | 5/2017 | Knight et al. |
| 2017/0370213 A1 | 12/2017 | Knight et al. |

FOREIGN PATENT DOCUMENTS

| | | |
|---|---|---|
| WO | 2015/103165 A1 | 7/2015 |
| WO | 2015/103332 A2 | 7/2015 |

OTHER PUBLICATIONS

International Written Opinion for International Application No. PCT/NL2016/050093 filed on Feb. 9, 2016 in the name of Biodentify B.V, dated Jun. 6, 2016. 6 pages.

Liao Xianyan et al "A new method of microbial prospecting for oil and gas based on BIOLOG metabolic fingerprinting analysis", Wei Sheng Wu Xue Bao—ACTA Microbiologica Sinica Apr. 4, 2012, vol. 52, No. 4, Apr. 4, 2012, pp. 505-511, XP008177703, ISSN: 0001-6209. 7 pages (English translation of Abstract Only).

Sofia Mosci et al. "Nonparametric Sparsity and Regularization", Massachusetts Institute of Technology—Computer Science and Artificial Intelligence Laboratory Technical Report, Sep. 26, 2011. 40 pages.

Corinna Cortes et al "Algorithms for Learning Kernels Based on Centered Alignment", Journal of Machine Learning Research 3 (2012) XX-XX, Submitted Jan. 2011; Published Mar. 2012. 35 pages.

\* cited by examiner

COMPUTER SUPPORTED EXPLORATION AND PRODUCTION OF HETEROGENEOUS DISTRIBUTED HYDROCARBON SOURCES IN SUBSURFACE FORMATIONS BASED ON MICROBIAL PROSPECTING

CROSS REFERENCE TO RELATED APPLICATIONS

The present application is the U.S. national stage of International Patent Application PCT/NL2016/050093 filed internationally on Feb. 9, 2016, which, in turn, claims priority to Dutch Patent Application No. 2014286 filed on Feb. 12, 2015.

TECHNICAL FIELD

The present invention relates to the oil and gas exploration and production industry, and more particularly, to an optimized exploration of heterogeneous distributed hydrocarbon sources in earth formations and the production thereof, such as the exploration and production of shale gas and shale oil sources, using microbial prospecting.

BACKGROUND

For an efficient production of a subsurface hydrocarbon source, reservoir engineers and exploration geoscientists aim to locate the best spots and trajectories for the wells to be drilled in and/or for the fracking of a shale formation.

Shale gas or oil formations, typically are heterogeneous formations whose mineralogy, organic content, natural fractures, and other properties vary from place to place with variations in the geological formations and rock properties.

A shale oil and/or shale gas play, in contrast to conventional oil and gas reservoirs or sources, which are generally more compact and limited in their areal surface and for which classical exploration and production techniques have proven to be effective, spreads over a large area.

A well drilled in a conventional oil and gas reservoir is capable of draining oil or gas over a relatively large area of the reservoir. In contrast, shale oil and shale gas plays require a number of relatively closely spaced wells, all of which are situated over the area of the shale oil and/or shale gas play, to produce the play successfully. Some of these wells produce significant larger volumes, i.e. highly productive wells or zones, also called 'sweet spots', compared to others, i.e. less productive wells or zones. Identification of the position of sweet spots before drilling and/or fracking will save considerable time and money, as drilling is preferably limited or essentially limited to the geographical location or zone indicative of and associated with the presence of a sweet spot at a shale oil and/or shale gas play.

Subsurface reservoirs are typically modelled from seismic and geological data obtained by geologists, geophysicists, and petrophysicists, using dedicated programmed computers and geostatistic modelling, for example. To produce shale sources identified by geostatistic modelling, in practice, a technique known as grid drilling is applied. That is, the area to be explored is overlaid by a virtual grid identifying geographic locations of the area. At a plurality or all of the grid positions wells are drilled to the shale formation and hydrocarbon productivity of such well is measured and expressed in a quantity indicative of the respective hydrocarbon productivity.

As well drilling is both time and cost consuming, in practice, production engineers aim to minimize drilling and/or fracking activities to the extend necessary for an efficient winning of oil or gas from an underground formation.

As an alternative for, or in addition to the seismic and geological data, in particular for detecting subsurface hydrocarbon sources, microbial prospecting may be used. It is known that certain bacteria respond to hydrocarbons, and hence may be used as indicators for finding oil and gas reservoirs.

Microbial prospecting for hydrocarbons is a surface exploration technique, based on the premise that volatile, gaseous hydrocarbon components such as methane (C1), ethane (C2), propane (C3) and butane (C4), for example, migrate upward from subsurface hydrocarbon accumulations through natural microcracks in geologic structures, generally called microseepage, and may affect microorganisms present in the shallow sub-soil ecosystem. Hydrocarbon-oxidizing bacteria exclusively use these gases as a carbon source for their metabolic activities and growth. These bacteria are typically found enriched in the soils/sediments above hydrocarbon bearing structures and may differentiate between hydrocarbon prospective and non-prospective productivity areas. That is, in terms of a shale gas or shale oil reservoir, between sweets spots and non- or low-productive zones, respectively.

The detection of various groups of methane, ethane, propane or butane oxidizing bacteria, for example, in the surface soils or sediments, helps to evaluate the prospects for hydrocarbon exploration and production.

Microbial prospecting essentially involves the collection of sub-soil samples from an area under investigation, followed by isolation and enumeration of microbial activity found in the samples. The microorganisms involved are not restricted to hydrocarbon-oxidizing or metabolising microorganisms, but may also include microorganisms that tolerate the volatile components, i.e. non-metabolising microorganisms, or microorganisms that are, to a certain extend, degraded or even eliminated by microseepage of volatile hydrocarbons.

Microorganisms present in samples of the surface soil or sediment taken from a play or area under investigation may be detected by microbiological screening techniques known in standard molecular biology techniques, providing microbial data identifying microorganisms, such as DNA sequences that serve as so-called biomarkers.

Analysing the microbial activity found, in terms of population density or bacterial count, for example, and applying a statistical approach and standard deviation value taken as a background value for the demarcation of anomalous zones, the results of the microbial analysis are presented on a geographical map of the area under investigation. This map serves the function of a predictive production map for drilling wells in the earth formations for the production of oil and/or gas.

For presalt hydrocarbon reservoirs, for example, at present, microbial prospecting appears to be a feasible exploration technique for prospecting the location of wells to be drilled to exploit an oil or gas source from such presalt reservoirs.

The results obtained by microbial prospecting may be integrated with other geoscientific and geophysical data to predict the hydrocarbon prospectivity of an area under investigation.

Although work on microbial prospecting has started in the early years of the twentieth century, and since then plural bacterial populations have been identified the presence and/or absence of which qualify for indicating the presence and/or absence of subsurface hydrocarbon sources, the effectiveness of microbial prospecting of heterogeneous subsurface hydrocarbon sources, such as shale gas and shale oil sources, still necessitates improvement. It is in particular the heterogeneity of a shale oil or gas play that makes exploration critical for maximizing production efficiency from such plays by minimizing the number of wells to be drilled.

SUMMARY

The invention relates to optimizing production of oil and/or gas from a heterogeneous distributed subsurface hydrocarbon source in an area or play under investigation, using microbial prospecting.

The invention also relates to optimizing exploration of a heterogeneous distributed subsurface hydrocarbon source in an area or play under investigation, prospecting the location of a well to be drilled or fracking to be applied in a subsurface formation by establishing a predictive production map indicative of predicted hydrocarbon productivity in the area or play under investigation.

As a starting point, for the purpose of the present invention, as elucidated in the background part above, one will appreciate that microbial prospecting techniques for obtaining microbial data representing a type and count of a plurality of different microorganisms representative of microbial activity attributable to microseepage in a geographical area or play comprising a subsurface hydrocarbon source or reservoir, are readily available in the art.

Accordingly, microbial data for the purpose of the present invention are assumed available and, for example, stored in a database associated with a computer or processing device, stored on a data carrier, or downloadable via a data connection from a remote digital database, or the like, or even made available by manually inputting same at in input of a computer or processing device.

The invention provides, in a first aspect, a computer supported or computer controlled method of exploring and producing a subsurface heterogeneous hydrocarbon source in an area under investigation, based on microbial prospecting, among others comprising microbial data representing a type and count of a plurality of different microorganisms representative of microbial activity. In sweet spots this microbial activity is attributable to hydrocarbon microseepage and different from the microbial activity in non- or low-productive zones of the area under investigation.

The method comprising the steps of:

i) retrieving, by the computer, of a plurality of geographic locations of an area or play comprising a heterogeneous hydrocarbon source, the microbial data associated with a quantity indicative of subsurface hydrocarbon productivity at a respective location;

ii) correlating, by the computer, in a data correlation algorithm, the retrieved microbial data and quantities indicative of hydrocarbon productivity, providing a threshold hydrocarbon productivity quantity and a truncated set of the retrieved microbial data, the set identifying individual types of the microorganisms and corresponding individual weighting factors computed by the data correlation algorithm, for distinguishing prospective hydrocarbon productivity quantities from non-prospective hydrocarbon productivity quantities;

iii) retrieving, by the computer, the microbial data of a further geographical location of an area under investigation;

iv) calculating, by the computer, an estimated subsurface hydrocarbon productivity quantity for the further geographical location by count weighting retrieved microbial data of this further location for microorganisms identified in the truncated set, applying the individual weighting factors, and v) producing or having produced the hydrocarbon source at the further geographical location if the estimated hydrocarbon productivity quantity compared to said threshold hydrocarbon productivity quantity qualifies as prospective hydrocarbon productivity quantity.

It has been found that by correlating, in a same data correlation algorithm, microbial data and productivity figures, i.e. quantities indicative of the hydrocarbon productivity at a respective one of a plurality of geographical locations of an area or play comprising a heterogeneous distributed hydrocarbon source, the hydrocarbon productivity of a further geographic location at an area under investigation can be reliably estimated from a truncated set of the correlated microbial data, identifying individual types of the microorganisms and corresponding individual weighting factors computed by the data correlation algorithm.

In practice, microbial data of a plurality of geographical locations are gathered by microbial prospecting, involving taking soil samples of the plurality of geographical locations and detecting microbial activity at each of these locations from the corresponding soil sample. The thus obtained microbial data, i.e. the different types of microorganisms or biomarkers found and the number or count of each such type or biomarker, are stored in a digital database or the like in association with a quantity or figure indicative of subsurface hydrocarbon productivity at or attributed to the respective location.

The plurality of geographic locations may comprise geographic locations of the area under investigation, i.e. microbial data and productivity data already known or estimated of such area and/or the plurality of geographic locations may comprises geographic locations of at least one known heterogeneous hydrocarbon play. For a known play, such productivity quantities are readily available, in particular of plays that have been investigated in accordance with the classical grid drilling exploration approach, as elucidated in the background part above.

It will be appreciated that such known microbial data and productivity data need to be gathered and stored only once.

By correlating the retrieved known microbial data and quantities indicative of hydrocarbon productivity in a data correlation algorithm, a threshold hydrocarbon productivity quantity is calculated and a truncated set of the thus correlated microbial data together with respective weighting factors. That is, the truncated set identifies a plurality of the microorganisms involved in the correlation and comprises for each type of microorganism in the set an individual weighting factor. The threshold value and the set of microorganisms and weighting factors is now available for distinguishing prospective hydrocarbon productivity quantities from non-prospective hydrocarbon productivity in an area under investigation.

The threshold quantity is calculated from the microbial data involved in the correlation as a whole, i.e. the type and count data of a respective microorganism and the corresponding productivity data, in particular the microbial data attributed to a sweet spot.

The composition of the truncated data set, i.e. the number and type of the different microorganisms or biomarkers involved, is subject to the composition of the available microbial data, the value of the computed individual weighting factors, the count of a particular microorganism or biomarker, the productivity quantity at the corresponding location and processing capacity of the computer or computers running the correlation algorithm. The composition of the truncated data set may be subject to selection by a user or automatically selected by the data correlation algorithm, whether or not based on user settable parameters as elucidated above.

In an example, the truncated set may involve about 50-250 different microorganisms or biomarkers contributing in a significant manner to the calculation of a hydrocarbon productivity quantity. In general, to a certain extend, a greater plurality of geographical locations involved in the correlation and/or larger truncated data set will produce more accurate results compared to a smaller data set and/or a lesser plurality of geographical locations. The data correlation algorithm balances accuracy and robustness of the truncated data set.

Data correlation algorithms suitable for the purpose of the present invention are one of a data regression algorithm, a data mining algorithm, a sparse approximation algorithm based on L1-regularization comprising kernel functions and robust parameter estimation by extensive cross validation. For the purpose of the present invention, the type of data algorithm to be applied may vary with the area to be investigated.

From the thus obtained truncated microbial data set and the individual weighting factors obtained, an estimated hydrocarbon productivity quantity of a further geographical location of an area under investigation is calculated by count weighting of the retrieved microbial data of this further location for those microorganisms or biomarkers identified in the truncated set.

That is, for each type of microorganism identified in the truncated set its count in the microbial data of the further location is weighted by the corresponding weighting factor, resulting in an estimated hydrocarbon productivity quantity or figure for the further location.

For hydrocarbon exploration of a hydrocarbon source in an area or play to be investigated, likewise, by microbial prospecting, microbial activity is detected at several geographical locations and stored in a digital database or the like. That is, microbial data of the area under investigation is obtained for at least those locations of which a productivity quantity is to be estimated.

By comparing the thus obtained estimated hydrocarbon productivity quantity and the calculated threshold hydrocarbon productivity, one may produce or have produced the hydrocarbon source at the area under investigation by drilling a well to the subsurface hydrocarbon source from this respective further geographical location, if the estimated hydrocarbon productivity quantity qualifies as a prospective hydrocarbon productivity quantity.

When calculating an estimated hydrocarbon productivity quantity for an area under investigation from microbial data and productivity quantities available of at least one known heterogeneous distributed hydrocarbon play, in particular a hydrocarbon play or area geographically different from the area under investigation, it has been found that, in a further embodiment, by correlating in a same data correlation algorithm both microbial data of the least one know heterogeneous hydrocarbon play and microbial data of at least one location of the area under investigation, associated with a known and/or assumed hydrocarbon productivity quantity or figure corresponding to the at least one location, the accuracy of an estimated productivity quantity, in particular the estimation of a sweet spot, in the area under investigation is significantly improved.

In the above further embodiment of the method, the at least one geographical location of the area under investigation is selected as comprising at least one geographical location at which a quantity indicative of subsurface hydrocarbon productivity at this location refers to absence or presence of high hydrocarbon production, i.e. the presence of a sweet spot.

Those skilled in the art will appreciate that for particular geologic formations one may validly assume that at certain locations or positions thereof hydrocarbon activity will be absent, i.e. the respective productivity quantity may be assumed zero. However, the productivity quantity of the at least one location of the area under investigation may be known, for example, from a (previous) well drilling operation, or may be readily estimated, for example, based on seismic and geological data obtained by geologists, geophysicists, and petrophysicists.

The accuracy of the estimated productivity quantities is, in another embodiment of the method, improved by repeating the steps for another geographical location of the area under investigation, wherein additionally microbial data and a measured quantity indicative of subsurface hydrocarbon productivity are retrieved of the further geographical location of which a calculated estimated hydrocarbon productivity quantity qualified as prospective. The data correlation is than performed for all microbial data and quantities indicative of hydrocarbon productivity retrieved. That is, the data of the known locations and data available of the area under investigation obtained from measuring the hydrocarbon productivity at a location the previously calculated estimated productivity quantity of which qualified as prospective.

In an yet further embodiment of the method, productivity quantities of the heterogeneous hydrocarbon source at the area under investigation are estimated for a plurality of (virtual) geographical grid positions of the area under investigation. That is, for each of the plurality of grid positions an estimated hydrocarbon productivity quantity is calculated by count weighting retrieved microbial data of a respective grid position for microorganisms identified in the truncated data set applying the individual weighting factors. From the results obtained, the hydrocarbon source at the area under investigation is produced or is having produced at a further geographical location comprised by a cluster of adjacent grid positions having estimated hydrocarbon productivity quantities qualifying as prospective hydrocarbon productivity quantities compared to the threshold hydrocarbon productivity quantity.

In particular for a heterogeneous distributed hydrocarbon source play, the location of a sweet spot is even more accurately predicted from a cluster of adjacent grid positions qualifying as prospective hydrocarbon productivity spots.

In the case of a subsurface heterogeneous distributed hydrocarbon source comprising at least one of a shale gas or shale oil source, producing or having produced the hydrocarbon source from the estimated productivity quantities calculated as prospective, comprises drilling a well to the subsurface shale source from the further geographical location, providing fracturing fluid into the well establishing fractures in the source or formation and extracting the shale gas or shale oil from the fractures.

Producing a shale source by fracturing is readily available to those skilled in the art and, for the purpose of the present invention, does not require further detailed specification.

In a second aspect the invention provides a computer supported or computer controlled method of generating a predictive production map of a subsurface heterogeneous hydrocarbon source in an area under investigation, based on microbial prospecting, among others comprising microbial data representing a type and count of a plurality of different microorganisms representative of microbial activity attributable to hydrocarbon microseepage. This predictive production map being indicative of predicted hydrocarbon productivity of the hydrocarbon source in the area under investigation.

The method comprising the steps of:

i) retrieving, by the computer, of a plurality of geographic locations of an area or play comprising a heterogeneous hydrocarbon source, the microbial data associated with a quantity indicative of subsurface hydrocarbon productivity at a respective location;

ii) correlating, by the computer, in a data correlation algorithm, the retrieved microbial data and quantities indicative of hydrocarbon productivity, providing a threshold hydrocarbon productivity quantity and a truncated set of the retrieved microbial data, the set identifying individual types of the microorganisms and corresponding individual weighting factors computed by the data correlation algorithm, for distinguishing prospective hydrocarbon productivity quantities from non-prospective hydrocarbon productivity quantities, iii) retrieving, by the computer, the microbial data of a plurality of geographical grid positions of the area under investigation;

iv) calculating, by the computer, an estimated subsurface hydrocarbon productivity quantity for each of the plurality of grid positions by count weighting retrieved microbial data of a respective grid position for microorganisms identified in the truncated set, applying the individual weighting factors, and v) providing, by the computer, the predictive production map by presenting the estimated hydrocarbon productivity quantities in relation to the corresponding grid positions of the area under investigation, and indicating whether an estimated hydrocarbon productivity quantity compared to the threshold hydrocarbon productivity quantity qualifies as prospective hydrocarbon productivity quantity.

It will be appreciated that, in practice, the grid positions are positions of a virtual grid, each position being indicated by its global positioning data, for example.

For completeness sake, it is noted that the data correlation algorithm may be any of the data correlation algorithms disclosed in respect of the method according to the first aspect of the invention.

The plurality of geographic locations involved in the correlation may comprise geographic locations of the area under investigation and/or the plurality of geographic locations may comprise geographic locations of at least one known heterogeneous hydrocarbon play, in particular a known heterogeneous distributed hydrocarbon play at an area geographically different from the area under investigation.

When estimating the hydrocarbon productivities in accordance with the second aspect of the invention based on microbial data and productivity figures of at least one known hydrocarbon play, in a further embodiment the accuracy of the predictive production map, i.e. the estimated productivity quantities, are significantly improved by retrieving, by the computer, further microbial data of at least one geographical location of the area under investigation, and by correlating in the same data correlation algorithm the further microbial data and a quantity indicative of subsurface hydrocarbon productivity at the at least one location of the area under investigation and the retrieved microbial data and quantities indicative of hydrocarbon productivity of the at least one known play.

The at least one geographical location of the area under investigation comprises at least one geographical location at which a quantity indicative of subsurface hydrocarbon productivity at this location refers to absence or presence of hydrocarbon production, based on at least one of assumed hydrocarbon productivity data, known hydrocarbon productivity data, and measured hydrocarbon productivity data obtained from well drilling at the at least one location.

In another embodiment of the method according to the second aspect, a refined predictive production map for the plurality of grid positions of the area under investigation is calculated by repeating the steps and wherein additionally microbial data and a measured quantity indicative of subsurface hydrocarbon productivity are retrieved of at least one grid position having an estimated hydrocarbon productivity quantity qualifying as a prospective hydrocarbon productivity quantity. The data correlation is than performed for all microbial data and quantities indicative of hydrocarbon productivity retrieved, thus the data of the known geographic locations of the area under investigation or of the known play or plays and the data available obtained from measuring the hydrocarbon productivity of at least one grid position the previously calculated estimated productivity quantity of which qualified as a prospective hydrocarbon productivity quantity.

In an embodiment, for illustrative purposes, the estimated hydrocarbon productivity quantities in relation to the corresponding grid positions of the area under investigation are graphically presented at an imaging device, including but not limited to a graphical display device, a computer screen or monitor, on paper, such that estimated hydrocarbon productivity quantities within a predefined range are identically presented, such as by an identical graphically distinguishable marking, for example one of a colouring, hatching and shading.

In this manner a clear predictive production map of the heterogeneous hydrocarbon source is provided, showing the contours of hydrocarbon productivity, and facilitating targeted well drilling for production of the hydrocarbon source. The productivity ranges corresponding to a particular marking may be selected, among others, based on the deviation in the calculated estimated productivity quantities, such to obtain an easy to read map.

The microbial data and productivity data for correlating purposes are, in accordance with the invention, preferably selected of at least one heterogeneous distributed hydrocarbon play having at least one property, and most preferably as much as possible properties in common with the area under investigation. Such properties include, but are not limited to: type of hydrocarbon source, i.e. a shale oil or shale gas source, whether the source is biogenic or non-biogenic, the geology, i.e. the organic content of the area such as (predominantly) clay, sand, stone or rock, the environment, like urban, grass land, farmland (grain), and water flows, ecology and climate, such as desert, wet land, artic, and the like.

For the purpose of the invention available DNA analysis techniques are readily commercially available, such as but not limited to DNA isolation based on the Qiagen DNeasy Plant Mini kit (cat no 69104 of Qiagen, Hilden, Germany), whether or not with an additional purification step by using Illustra autoscreen 96A well plates (GE Healthcare, Pittsburgh, Pa., USA), or DNA isolation based on the MoBio PowerSoil htp DNA isolation kit (cat no 12955-12), and equivalents.

Although the methods disclosed above have proven to be successful for subsurface heterogeneous shale gas or shale oil sources, the methods may be used for an area under investigation comprised by a pre salt area and below a sea or lake, for example.

In a third aspect, the invention provides a system comprising at least one computer and data input/output equipment, the computer being communicatively connected or connectable to a database among others storing, of a plurality of geographic locations of an area or play comprising a heterogeneous hydrocarbon source, microbial data representing a type and count of a plurality of different microorganisms representative of microbial activity attributable to hydrocarbon microseepage and respective quantities indicative of subsurface hydrocarbon productivity of a respective location, the at least one computer being arranged for performing the computer implemented steps of any of the methods disclosed above.

In an embodiment of the system the database stores microbial data and quantities indicative of subsurface hydrocarbon productivity of an area under investigation comprising a subsurface heterogeneous hydrocarbon source.

In another embodiment, the database stores microbial data and quantities indicative of subsurface hydrocarbon productivity of at least one known heterogeneous distributed hydrocarbon play.

In a fourth aspect, the invention provides a computer program product downloadable from a communication network and/or stored on a computer-readable and/or processor-executable medium, the computer program product comprising program code instructions to cause a computer to carry out the computer implemented steps of any of the methods disclosed above. Non-transitory computer readable or processor-executable media for the purpose of to invention include but are not limited to any of optically, magnetically, solid state semiconductor or other media, such as designated Compact Discs, CDs, Digital Versatile Disks, DVDs, flash memory, memory sticks, Hard Disk Drives, HDDs, Solid State Drives, SDDs, etc.

The above-mentioned and other features and advantages of the invention are illustrated in the following description with reference to the enclosed drawings which are provided by way of illustration only and which are not limitative to the present invention.

DETAILED DESCRIPTION

Figure 1:
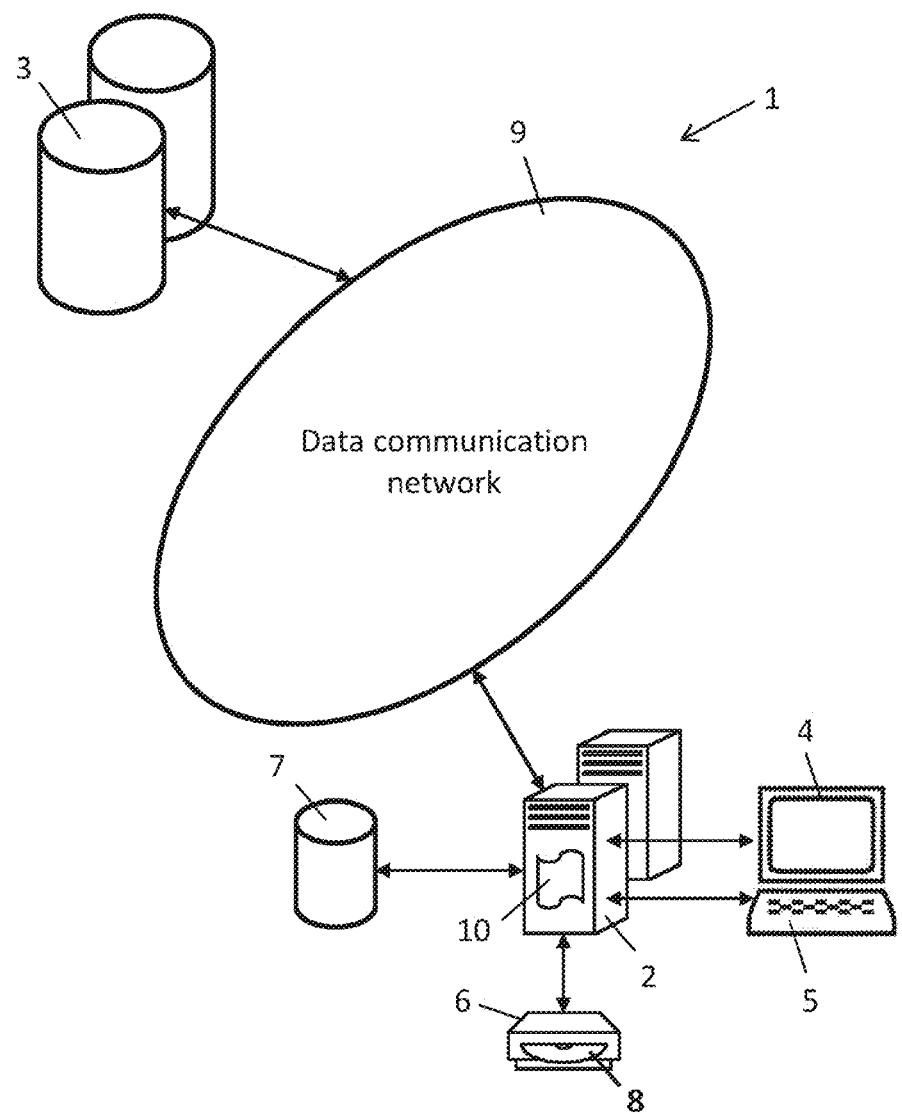
FIG. 1 shows, in a schematic and illustrative manner, a block diagram of a computer system arranged in accordance with the invention.

FIG. 1 illustrates in a simplified block diagram a computer system 1 comprising at least one digital computer or data processing equipment 2 and a remote digital data storage facility comprised of one or a plurality of databases 3. The computer or data processing equipment 2 connects or is connectable to the remote data storage facility or databases 3 via an intermediate data communication network 9, such as the internet or any other generally available wired or wireless data communication network. It will be appreciated that the computer or processing equipment 2 and the data storage facility or databases 3 are provided with data communication equipment facilitating data transfer, among others data retrieval, with the data storage facility or databases 3 by the computer or processing equipment 2.

The computer or data processing equipment 2 further connects to data input/output equipment 4, 5, 6, among others comprising a display 4, keyboard 5 and data transfer equipment 6 for reading and/or writing data to a computer readable data storage medium 8, such a CD, DVD, flash memory, memory stick, HDD, SDD, etc. The computer readable storage medium 8 may comprise a computer-readable and/or processor-executable medium, storing a computer program product comprising program code instructions to cause a computer to carry out the computer implemented steps in accordance with the invention. Alternative or in addition to the remote data storage facility or databases 3, the computer or processing equipment 2 may connect or may comprise a local data base 7.

The data input/output equipment 4, 5, 6 may be integral with or connectable to the computer or processing equipment 2 via the data communication network 9 in the case of input/output equipment 4, 5, 6 taking the form of a tablet or personal or laptop computer, for example. In such a case, the computer or processing equipment 2 may take the form of one or a plurality of remote servers, arranged for retrieving and processing big data volumes.

For the purpose of the invention, in use, the data storage facility or databases 3 store microbial data representing a type and count of a plurality of different microorganisms representative of microbial activity attributable to hydrocarbon microseepage of a plurality of geographic locations of an area under investigation and/or of at least one known heterogeneous hydrocarbon play and respective quantities indicative of subsurface hydrocarbon productivity of the plurality of locations. In a practical embodiment of the invention, the data storage facility or databases 3 store microbial data and associated productivity data of as much as six known heterogeneous shale oil producing plays, or even more.

Microbial data obtained from an area under investigation, that are the types and bacterial count obtained from DNA analyses of a sub-soil sample taken at one or a plurality geographic locations at the area under investigation and representative of microbial activity influenced by microseepage, may also be stored in the data storage facility or databases 3 in association with productivity quantities or figures, if available. It will be appreciated that relevant microbial data and productivity data may, for example, also be directly stored or downloaded in the local database 7 connected to the computer or processing equipment 2, whereas measured productivity quantities may be inputted through the input/output means, such as the keyboard 5 or data transfer equipment 6, for example.

Reference numeral 10 designates a data correlation algorithm running at the computer or processing equipment 2 for correlating, by the computer or processing equipment 2, microbial data and quantities indicative of hydrocarbon productivity of at least one known play and of the area under investigation, retrieved by the computer or processing equipment 2 from the data storage facility or databases 3 and/or the local database 7 and/or retrieved after manual input of respective data from an of the input/output means 4, 5, 6, for example.

The data correlation algorithm 10, in accordance with the invention, is arranged for calculating a threshold quantity distinguishing prospective hydrocarbon productivity quantities from non-prospective hydrocarbon productivity quantities in the area under investigation. That is, separating sweet spots from zones with none or low productivity compared to a sweet spot.

The data correlation algorithm is further arranged to calculate distinguishable biomarkers and their individual weighting factors for the different types of microorganisms or biomarkers available in the microbial data retrieved, i.e. the microbial data available of the area under investigation and/or of at least one known play. In an advanced data processing, these weighting factors are calculated from microbial data gathered at a plurality of geographic positions and at a number of different known heterogeneous distributed hydrocarbon plays, in respect of the count or number of a particular type of microorganism or biomarker detected at a respective location and the known hydrocarbon productivity quantity or figure associated with that respective location. That is, known plays different compared to the area under investigation.

When using, with the data correlation algorithm 10, only microbial data and productivity data of known plays, for calculating estimated productivity quantities with increased accuracy in an embodiment of the invention, microbial data of at least one location of the area under investigation have to be made available in association with a hydrocarbon productivity quantity corresponding to the at least one location.

The at least one location is selected such as being a location the hydrocarbon productivity quantity of which is known, for example from a (previous) well drilling operation, or can be readily estimated, for example based on known seismic and geological data of the area under investigation. Those skilled in the art will appreciate that for particular geologic formations one may validly assume that at certain locations or positions thereof hydrocarbon activity will be absent, i.e. the respective productivity quantity may be assumed zero.

Data correlation algorithms 10 for the purpose of the invention are, for example, designated sparse approximation algorithm based on L1-regularization comprising kernel functions and robust parameter estimation by extensive cross validation, described in "Nonparametric Sparsity and Regularization", by Sofia MOSCI et al., Sep. 26, 2011, Massachusetts Institute of Technology, Cambridge, USA, and the Journal of Machine Learning Research 3 (2010), published Dec. 3, 2012, "Algorithms for Learning Kernels based on Centered Alignment", by Corinna CORTES et la. However, other data correlation algorithms may be applied, such as one of a data regression algorithm and a data mining algorithm, for example, and equivalents.

The correlating step of the invention provides a threshold quantity and a microbial based, hydrocarbon production predictive model, comprised of a truncated set of the correlated microbial data and individual weighting factors.

The truncated set, in an example, may be provided as a list of distinguishable individual biomarkers or microorganisms, for example identified by an identifier i, and a corresponding individual weighting factor $\lambda_i$. The threshold quantity is calculated such to identify hydrocarbon productivity quantities qualifying as prospective hydrocarbon productivities, i.e. pointing to a sweet spot.

The threshold quantity and the truncated, i.e. the distinguishable, microbial data set, i.e. the amount of microorganisms or biomarkers involved for calculating an estimated productivity quantity in accordance with the invention, depends, among others, from the composition of the available microbial data, the number of known plays involved, the value of the computed weighting factors, the count of a particular microorganism or biomarker, the productivity quantity at the corresponding location. The composition of the truncated data set may be subject to user selection or automatically selected by the data correlation algorithm, whether or not based on user settable parameters, for example based on available processing capacity of the computer or computers running the correlation algorithm and available processing time.

From computer simulations, it has been observed that a model, i.e. a truncated data set, applying a relatively large number of distinguishable biomarkers, such as more than 50 biomarkers, for example, already comprises a lot of detail and hence is able to even predict small differences between different plays.

The individual weighting factors $\lambda_i$ may have a positive or negative value, i.e. determining whether a certain microorganism or biomarker adds in a positive or negative manner to the calculated quantity. The exact value of the threshold quantity depends on a case by case basis. In the specific example of the model above, productivity quantities above the threshold quantity point to prospective hydrocarbon productive locations such that the more above the threshold, the more a quantity refers to a sweet spot.

With thus obtained truncated set or hydrocarbon production predictive model, productivity quantities or figures of any further location at the area under investigation can be estimated. Such an estimated quantity is calculated by the computer or processing equipment 2 from retrieved microbial data available or established for the respective further location in accordance with:

$$Q = \sum_{n=1}^{x} (\lambda_1 \alpha_1 + \lambda_2 \alpha_2 + \ldots + \lambda_i \alpha_i + \ldots + \lambda_x \alpha_x)$$

wherein:
Q=estimated quantity
$\lambda_i$=individual weighting factor for microorganism of type i
x=number of distinguishable microorganisms of the truncated set
$\alpha_i$=count of microorganism of type i.

That is, the productivity quantity at the further location of the area under investigation is estimated by count weighting of the retrieved microbial data of the further location for those microorganisms present in the retrieved microbial data of the further location and identified by the truncated set, as expressed by the equation. For clarity sake, in all the microbial data applied, like microorganisms or biomarkers are uniquely identified.

With the method according to the invention, reservoir engineers and exploration engineers are able to predict drilling locations, such as sweet spots, more accurately. If the estimated hydrocarbon productivity quantity compared to the threshold hydrocarbon productivity quantity qualifies as prospective hydrocarbon productivity quantity, production engineers may decide to produce or have produced the hydrocarbon source at the further geographical location.

As discussed in the summary part above, besides extending the correlation step by involving microbial data of plural known plays, the prediction accuracy of the method according to the invention may be further enhanced by involving in the correlation algorithm microbial data and productivity figures of a plurality of locations of the area under investigation. For example, productivity quantities or figures obtained from well drilling measurements at the area under investigation at locations previously identified by the method as prospective locations.

The prediction results of the method according to the invention are best illustrated by Table 1 illustrating the prediction accuracy of the method according to the invention, based on microbial data and production quantities of a plurality of known heterogeneous hydrocarbon plays, indicated in the left-hand column of Table 1, and all located in the USA.

For illustrative purposes, microbial data and productivity quantities of 30% of the available geographic locations of each play are deliberately not included in the correlation algorithm. These locations are used for checking the prediction accuracy of the invention and are randomly selected. The remainder 70% of the available data is used for data correlation purposes, i.e. serves as starting database.

TABLE 1

Normalized prediction scores.

| | Using no data of area under investigation | Using one non-productive location of area under investigation | Using (#) locations of area under investigation |
|---|---|---|---|
| Kentucky, Big Sandy, Marcellus | 0.80 | 0.84 | 0.95 (10) |
| Michigan, Antrim | 0.52 | 0.71 | 0.91 (24) |
| New Mexico, Lewis | 0.70 | 0.80 | 0.93 (27) |
| Louisiana, Haynesville | 0.60 | 0.81 | 0.94 (25) |
| Texas, Avalon and Bone Spring | 0.71 | 0.82 | 0.93 (18) |
| North Dakota, Bakken | 0.60 | 0.78 | 0.91 (23) |

Suppose the New Mexico Lewis play acts as the area under investigation. In a first step only the remainder 70% of the microbial data and productivity quantities of the remainder plays are correlated, not using any data of the New Mexico Lewis play, resulting in a truncated data set of the microbial data and individual weighting factors for each of the biomarkers identified in the truncated set.

In a second step, an estimated subsurface hydrocarbon productivity quantity for a geographical location of the New Mexico Lewis play is estimated, by count weighting retrieved microbial data of this location for the microorganisms identified in the truncated set, applying the individual weighting factors obtained from the data correlation.

The above first and second steps are repeated 1000 times for different compositions of the starting database and different geographic locations of the New Mexico Lewis play, providing 1000 estimated hydrocarbon productivity quantities for 1000 locations of the New Mexico Lewis play.

The thus estimated hydrocarbon productivity quantities are compared with the known productivity quantities of the corresponding locations of the New Mexico Lewis play. The averaged normalized prediction score of correctly estimated productivity quantities is shown in the column of table 1 headed: "Using no data of area under investigation".

The above is successively repeated for all of the plays identified in Table 1, while each time not using any microbial data and production quantities of a respective play.

Again suppose the New Mexico Lewis play acts as the area under investigation. Next, in accordance with the invention, microbial data and a production quantity of one location of the New Mexico Lewis play, i.e. the particular area under investigation, not referring to a sweet spot, are included in the correlation algorithm, together with the microbial data and productivity quantities of the starting database, as explained above. The result is a further truncated data set of the microbial data and further individual weighting factors for each of the biomarkers identified in the truncated set.

Subsequently, an estimated subsurface hydrocarbon productivity quantity for a further geographical location of the New Mexico Lewis play not used in the correlation algorithm is calculated by count weighting retrieved microbial data of this further location for the microorganisms identified in the further truncated set, and applying the further individual weighting factors obtained from the data correlation, as explained above.

Again, these steps are repeated 1000 times for different compositions of the starting database and different further geographic locations of the New Mexico Lewis play, providing 1000 estimated hydrocarbon productivity quantities for 1000 further locations of the New Mexico Lewis play.

The thus estimated hydrocarbon productivity quantities are again compared with the known productivity quantities of the corresponding locations of the New Mexico Lewis play. The averaged normalized prediction score of correctly estimated productivity quantities is shown in the column of Table 1 headed: "Using one non-productive location of area under investigation".

The prediction for the New Mexico Lewis play is likewise repeated for any other of the known plays acting as area under investigation.

The right-hand column of Table 1, headed "Using (#) locations of area under investigation" indicates the prediction accuracy of the method according to the invention when involving in the correlation algorithm microbial data and corresponding productivity quantities of a number # of locations as indicated between brackets. For the New Mexico Lewis play, i.e. the area under investigation, for example, 27 locations have been involved referring to sweet spots and none or low productivity locations.

As can be viewed from Table 1, not including in the correlation algorithm microbial data and productivity quantities of at least one location of the area under investigation, in case of the New Mexico Lewis play acting as the area under investigation, results in a prediction score of 0.70.

However, by including in the correlation algorithm, in accordance with the invention, microbial data and a corresponding productivity quantity of at least one location of the area under investigation, the prediction accuracy for the New Mexico Lewis play increases with over 14% from 0.70 to 0.80. By including in the correlation algorithm data of further locations of the area under investigation, the prediction accuracy for the Texas Avalon play even increases with over 32% from 0.70 to 0.93.

Similar observations can be made for the other plays indicated in Table 1, and very high prediction accuracies up to 0.95 are observed.

In the calculations leading to the scores indicated in Table 1, the truncated set of biomarkers or microorganisms varied in accordance with the microbial data population involved in the correlation, and comprised 50-200 different biomarkers out of set of, for example, over 140.000 biomarkers obtained by DNA analysis.

The prediction accuracy is, among others, subject to the number of different biomarkers admitted in the truncated data set. In a practical case, one may vary the number of the biomarkers, for example, while observing the variation in the estimated productivity quantity of the area under investigation. Once the variation is not statistically significant, one may validly assume that the truncated model comprises sufficient biomarkers for an accurate prediction. An analogues approach may be applied to the number of iterations and the number of locations of the area under investigation involved in the correlation algorithm.

Figure 2:
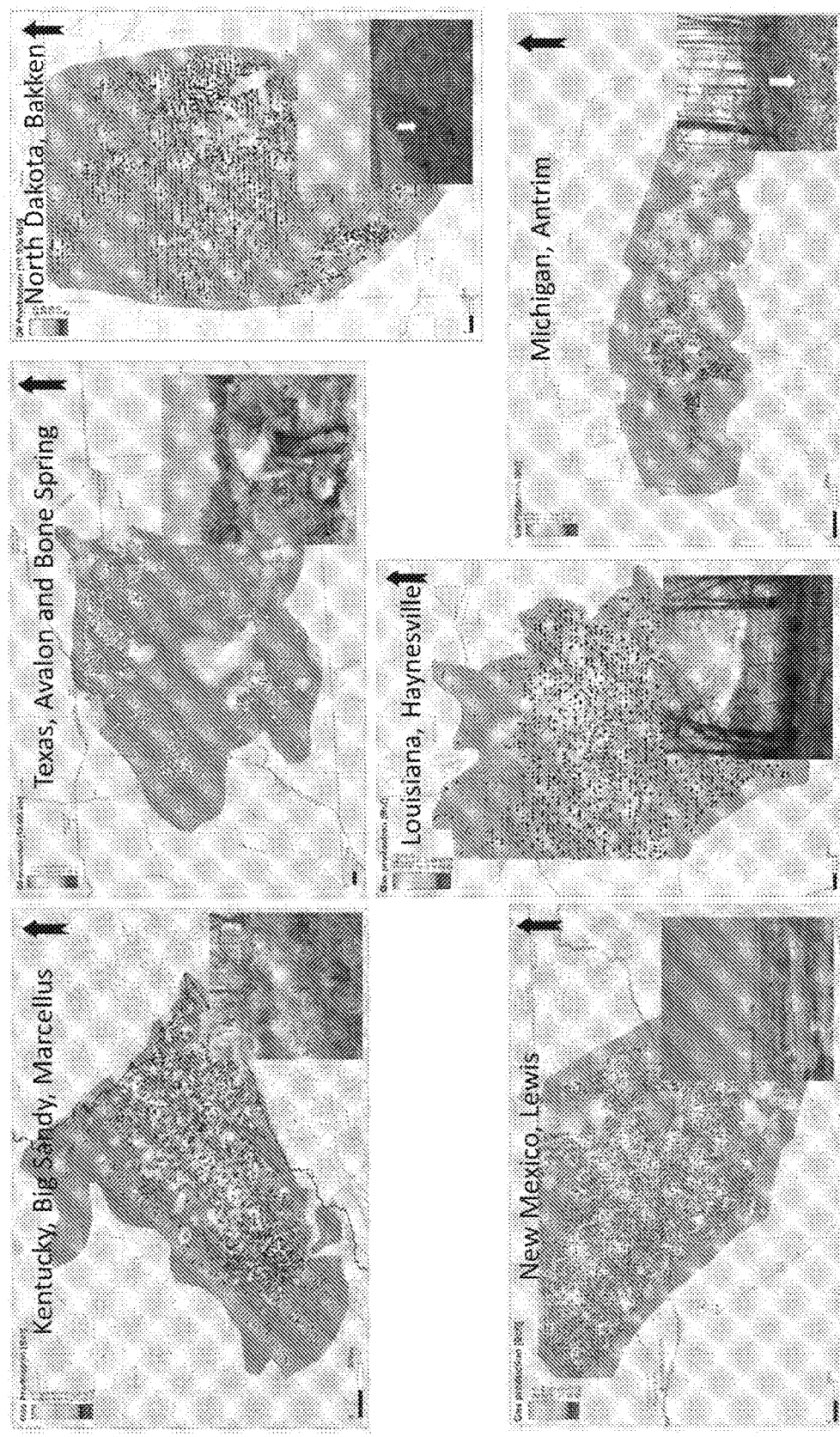
FIG. 2 shows, in a graphic representation, several known plays for use in the method according to the invention.

FIG. 2 shows, in a graphic representation, known plays as referred to in Table 1, the microbial data and productivity quantities or figures of which at the black or white spots or dots are known and available in a database for the use in the present invention. The photographic inserts at the respective plays are characteristic for the vegetation, landscape and climate at a particular play.

In summary, the Kentucky Big Sandy shale gas field is an outlier of the well-known Marcellus Shale. The Big Sandy shale can be characterised as having locations situated in forest areas with grass, grasslands and along riverbanks. The Antrim Shale, located in the northern part of the State of Michigan, consist of forest debris and farmlands. Soils are mainly sandy, some clay and a few pebbles. The Lewis shale is situated in the San Juan basin in the State of New Mexico and is the largest producer of natural gas in this Rocky Mountain state. Gas is produced from offshore-marine shales, mudstones, siltstones, and sandstones of the Lewis Shale and marginal marine shoreface sandstones and siltstones of both the La Ventana Tongue and the Chacra Tongue of the Cliff House Sandstone. Soils are mainly rocky and sandy. The Texas Avalon and Bone Spring shale field is a combined field in the south eastern part of the State of New Mexico, in the Permian basin. The Avalon shale is a small shale oil play that is also known as the Leonard Shale. The Bone Spring shale is also an oil play and consists of multi-pay reservoirs. Soils are mainly rocky and sandy, i.e. a desert environment. The Haynesville Shale, found in Texas and Louisiana, is an Upper Jurassic shale play and is characterised by both forest and farm land and urban areas. It has a hot and moist climate. Soils are grey to red in colour as well as sandy. The North Dakota Bakken shale is the most well-known shale oil play and is one of the largest continuous oil accumulations in the world. The area comprises grass land, farmlands (grain), and water flows. Soil consists of clays, sand and pebbles.

In the graphic presentations or production maps shown in FIG. 2, the lighter gray zones indicate production spots, in accordance with the production scale depicted at the left upper corner of a respective map.

FIGS. 3, 4, 5 and 6 illustrate, in a schematic and graphical manner, the generation of a predictive production map of a subsurface heterogeneous hydrocarbon source in an area under investigation, in accordance with the second aspect of the invention.

The area under investigation 20 is completely or partly overlaid by a virtual grid 21, indicating locations that qualify for microbial prospecting, i.e. locations of which microbial data are to be obtained by taking sub-soil samples and analysing the microbial activity of each such sample, using DNA analysis as previously disclosed. The microbial data thus obtained are store, for example, in the data storage facility or databases 3 shown in FIG. 1, together with the microbial data and productivity data available from at least one known play.

Figure 3:
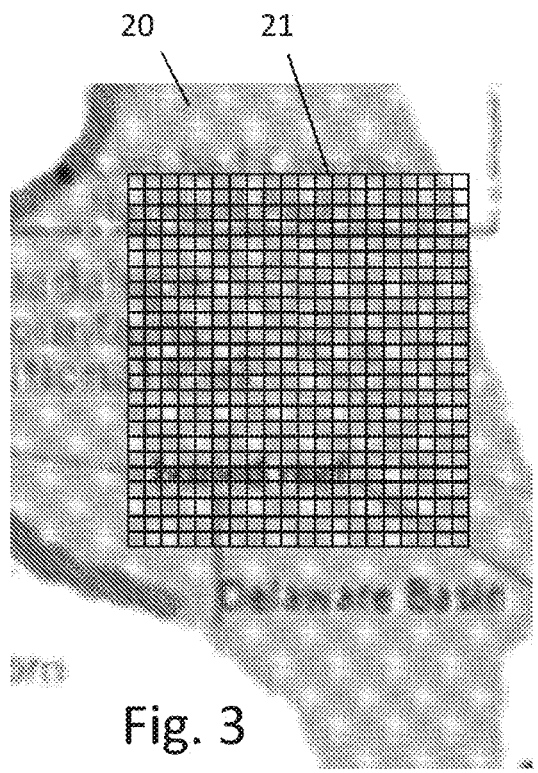
FIGS. 3, 4, 5 and 6 illustrate, in a graphic representation, the generation of a predictive production map of a subsurface heterogeneous hydrocarbon source in an area under investigation.
Figure 4:
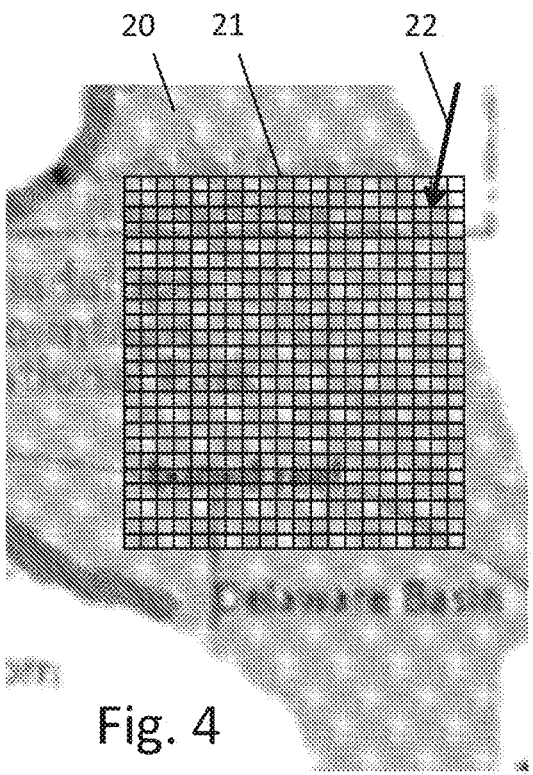

FIG. 3 shows the area under investigation 20 and the overlaid grid 21. It will appreciated that each grid position may be identified in a well-known global coordinate system. From the respective global positioning data, the locations for collecting samples can be easily identified in the area using suitable global positioning indication means.

According to an embodiment of the invention, for at least one location of the area under investigation 20 and indicated by a position of the grid 21, a productivity quantity or figure is obtained. In this example, a position near the edge of the area under investigation is selected, as indicated by arrow 22 in FIG. 4. One may validly assume that hydrocarbon productivity at the location 22 is minimal, i.e. zero or close to zero.

The thus obtained data are stored in the storage facility or databases 3, or the local database 7, for example, and retrieved by the computer 3 for being processed by the correlation algorithm 10 in conjunction with the microbial data and productivity data retrieved of the known play or plays.

As disclosed above, the correlating step provides a microbial based, hydrocarbon production predictive model, comprised of a truncated set of the correlated microbial data and individual weighting factors, and a threshold quantity.

For each or a plurality of the grid positions, using the thus obtained predictive model, hydrocarbon productivity quantities are estimated from the available microbial data of a respective grid position.

A predictive production map is generated by presenting the estimated hydrocarbon productivity quantities in relation to the corresponding grid positions of the area under investigation, and indicating whether an estimated hydrocarbon productivity quantity compared to the threshold hydrocarbon productivity quantity qualifies as prospective hydrocarbon productivity quantity.

Figure 5:
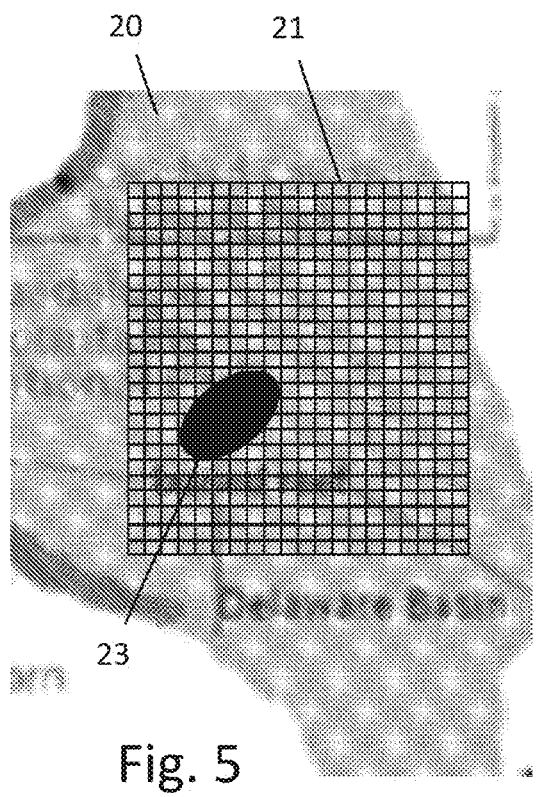
Figure 6:
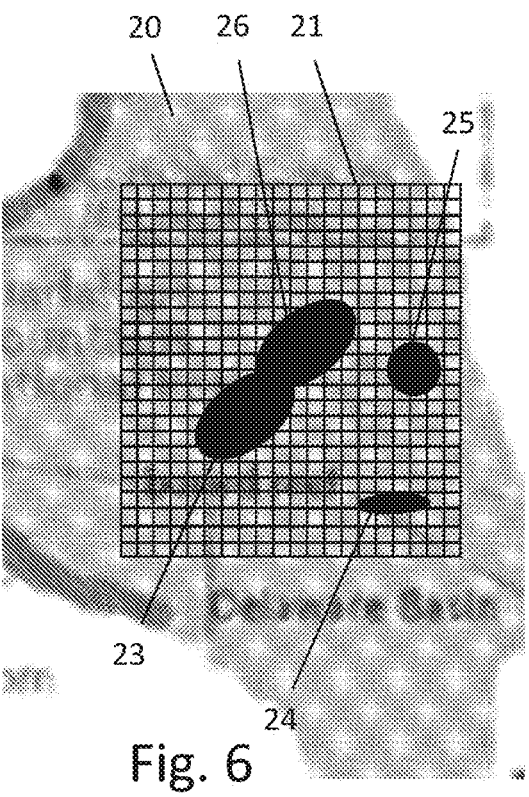

FIG. 5 shows a production map indicating a predicted sweet spot 23, for example. Estimated hydrocarbon productivity quantities within a predefined range may be identically presented at the production map, such as by an identical graphically distinguishable marking comprising one of a colouring, hatching and shading, resulting in predictive production contours as shown in FIG. 2, for example.

The predictive production map may be further refined from drilling a well to the hydrocarbon source at a location corresponding to a predicted sweet spot and measuring the productivity quantity. Applying the thus obtained productivity data in the data correlation algorithm, the production predictive model is refined. Using this refined model, further prospective locations can be found, such as indicated by reference numerals 24, 25, 26 shown in FIG. 6. The predictive production map can be further refined by drilling a well at respective grid locations corresponding to a prospective location 24, 25, 26 and measuring corresponding productivity quantities. The predictive model can be further refined by using the measured quantities in the correlation algorithm, and so on.

Those skilled in the art will appreciate that grid prediction may also be used in the first aspect of the invention, for locating prospecting zones in the area under investigation.

The invention may be practiced otherwise than as specifically described herein, and the above mentioned embodiments and examples are merely intended as an illustration to the skilled reader. In particular, estimated productivity quantities of the area under investigation may be derived from running the correlation algorithm for different microbial data and applying statistical analyses of the results obtained.

The invention claimed is:

1. A computer supported method of exploring and producing a subsurface heterogeneous hydrocarbon source in an area under investigation, based on microbial prospecting, comprising microbial data representing a type and count of each type of a plurality of different microorganisms representative of microbial activity attributable to hydrocarbon microseepage, said method comprising the steps of:

i) retrieving, by said computer, of a plurality of geographic locations of an area or play comprising a heterogeneous hydrocarbon source, said microbial data associated with a quantity indicative of subsurface hydrocarbon productivity at a respective location;

ii) correlating, by said computer, in a data correlation algorithm, said retrieved microbial data and quantities indicative of hydrocarbon productivity, providing a threshold hydrocarbon productivity quantity and a truncated set of said retrieved microbial data, said set identifying individual types of said microorganisms and corresponding individual weighting factors computed by said data correlation algorithm, for distinguishing prospective hydrocarbon productivity quantities from non-prospective hydrocarbon productivity quantities, iii) retrieving, by said computer, said microbial data of a plurality of geographical grid positions of an area under investigation;

iv) calculating, by said computer, an estimated subsurface hydrocarbon productivity quantity for each of said geographical grid positions by count weighting retrieved microbial data of a respective geographical grid position for microorganisms identified in said truncated set, applying said individual weighting factors, wherein the estimated subsurface hydrocarbon productivity quantity is calculated as $$Q=(\lambda_1\alpha_1+\lambda_2\alpha_2+\ldots+\lambda_i\alpha_i+\ldots+\lambda_x\alpha_x)$$

where Q is the estimated subsurface hydrocarbon productivity quantity, $\lambda_i$ is an individual weighing factor of microorganism type i, x is the number of microorganisms identified in the truncated set, and $\alpha_i$ is a count of microorganism of type i, and v) producing said hydrocarbon source at said area under investigation at a further geographical location thereof comprising a cluster of adjacent grid positions having estimated subsurface hydrocarbon productivity quantities qualifying as prospective hydrocarbon productivity quantities compared to said threshold hydrocarbon productivity quantity.

2. The method according to claim 1, wherein said plurality of geographic locations comprises geographic locations of said area under investigation.

3. The method according to claim 1, wherein said plurality of geographic locations comprises geographic locations of at least one known heterogeneous hydrocarbon play.

4. The method according to claim 1, wherein said plurality of geographic locations comprises geographic locations of at least one known heterogeneous hydrocarbon play, said retrieving in step i) further comprises retrieving, by said computer, of at least one geographical location of said area under investigation, said microbial data and a quantity indicative of subsurface hydrocarbon productivity at said location, and wherein said correlating in step ii) comprises correlating said retrieved microbial data and quantities indicative of hydrocarbon productivity of said at least one known play and said area under investigation.

5. The method according to claim 1, wherein said retrieving in step i) further comprises retrieving, by said computer, of at least one geographical location of said area under investigation, said microbial data and a quantity indicative of subsurface hydrocarbon productivity at said location, said at least one geographical location of said area under investigation comprises at least one geographical location at which a quantity indicative of subsurface hydrocarbon productivity at said location refers to absence or presence of hydrocarbon production based on at least one of: assumed hydrocarbon productivity data, known hydrocarbon productivity data, and measured hydrocarbon productivity data obtained from well drilling at said at least one location.

6. The method according to claim 1, wherein said plurality of geographic locations comprises geographic locations of at least one known heterogeneous hydrocarbon play, said at least one heterogeneous hydrocarbon play is selected based on at least one property in common with said area under investigation of a plurality of properties including: type of hydrocarbon source, biogenic and non-biogenic, geology, environment, ecology and climate.

7. The method according to claim 1, wherein steps i) -v) are repeated for said area under investigation in step iii), wherein said retrieving in step i) additionally comprises retrieving, by said computer, said microbial data and a measured quantity indicative of subsurface hydrocarbon productivity of said further geographical location of said area under investigation having estimated hydrocarbon productivity quantities qualifying as prospective hydrocarbon productivity quantities in accordance with step iv), and wherein step ii) is performed for all said microbial data and quantities indicative of hydrocarbon productivity retrieved in step i).

8. The method according to claim 1, wherein said subsurface heterogeneous hydrocarbon source comprises at least one of a shale gas or shale oil source, wherein producing said hydrocarbon source comprises drilling a well to said subsurface shale source from said further geographical location, providing fracturing fluid into said well establishing fractures in said source and extracting said shale gas or shale oil from said fractures.

9. A system comprising at least one computer and data input/output equipment, said computer being communicatively connected or connectable to a database among others storing, of a plurality of geographic locations of an of an area or play comprising a heterogeneous hydrocarbon source, microbial data representing a type and count of a plurality of different microorganisms representative of microbial activity attributable to hydrocarbon microseepage and quantities indicative of subsurface hydrocarbon productivity at a respective location, said at least one computer being arranged for performing said computer implemented steps of claim 1.

10. The system according to claim 9, wherein said database stores microbial data and quantities indicative of subsurface hydrocarbon productivity of an area under investigation comprising a subsurface heterogeneous hydrocarbon source.

11. The system according to claim 9, wherein said database stores microbial data and quantities indicative of subsurface hydrocarbon productivity of at least one known heterogeneous hydrocarbon play.

12. A computer program product downloadable from a communication network and/or stored on a computer-readable and/or processor-executable medium, said computer program product comprising program code instructions to cause a computer to carry out said computer implemented steps of claim 1.

13. The method according to claim 1, wherein said area under investigation is a pre salt area.

14. The method according to claim 1, wherein said microbial data are obtained from DNA analyses of soil samples taken at particular geographical position, and stored in a computer accessible database in association with respective hydrocarbon productivity quantities.

15. The method according to claim 1, wherein said data correlation algorithm is one of a data regression algorithm, a data mining algorithm, a sparse approximation algorithm based on L1-regularization comprising kernel functions and robust parameter estimation by extensive cross validation.

16. A computer supported method of providing a predictive production map of a subsurface heterogeneous hydrocarbon source in an area under investigation, based on microbial prospecting, comprising microbial data representing a type and count of each type of a plurality of different microorganisms representative of microbial activity attributable to hydrocarbon microseepage, said predictive production map being indicative of predicted hydrocarbon productivity of said hydrocarbon source in said area under investigation, said method comprising the steps of:
  i) retrieving, by said computer, of a plurality of geographic locations of an area or play comprising a heterogeneous hydrocarbon source, said microbial data associated with a quantity indicative of subsurface hydrocarbon productivity at a respective location;
  ii) correlating, by said computer, in a data correlation algorithm, said retrieved microbial data and quantities indicative of hydrocarbon productivity, providing a threshold hydrocarbon productivity quantity and a truncated set of said retrieved microbial data, said set identifying individual types of said microorganisms and corresponding individual weighting factors computed by said data correlation algorithm, for distinguishing prospective hydrocarbon productivity quantities from non-prospective hydrocarbon productivity quantities,
  iii) retrieving, by said computer, said microbial data of a plurality of geographical grid positions of said area under investigation;
  iv) calculating, by said computer, an estimated subsurface hydrocarbon productivity quantity for each of said plurality of grid positions by count weighting retrieved microbial data of a respective grid position for microorganisms identified in said truncated set, applying said individual weighting factors, wherein the estimated subsurface hydrocarbon productivity quantity is calculated as $$Q=(\lambda_1\alpha_1+\lambda_2\alpha_2+\ldots+\lambda_i\alpha_i+\ldots+\lambda_x\alpha_x)$$

where Q is the estimated subsurface hydrocarbon productivity quantity, $\lambda_i$ is an individual weighing factor of microorganism type i, x is the number of microorganisms identified in the truncated set, and $\alpha_i$ is a count of microorganism of type i, and
  v) providing, by said computer, said predictive production map by presenting said estimated hydrocarbon productivity quantities in relation to said corresponding grid positions of said area under investigation, and indicating a further geographical location comprising a cluster of adjacent grid positions having estimated subsurface hydrocarbon productivity quantities qualifying as prospective hydrocarbon productivity quantities compared to said threshold hydrocarbon productivity quantity.

17. The method according to claim 16, wherein said plurality of geographic locations comprises geographic locations of said area under investigation.

18. The method according to claim 16, wherein said plurality of geographic locations comprises geographic locations of at least one known heterogeneous hydrocarbon play.

19. The method according to claim 18, wherein said plurality of geographic locations comprises geographic locations of at least one known heterogeneous hydrocarbon play, said retrieving in step i) further comprises retrieving, by said computer, of at least one geographical location of said area under investigation, said microbial data and a quantity indicative of subsurface hydrocarbon productivity at said location, and wherein said correlating in step ii) comprises correlating said retrieved microbial data and quantities indicative of hydrocarbon productivity of said at least one known play and said area under investigation.

20. The method according to claim 19, wherein said retrieving in step i) further comprises retrieving, by said computer, of at least one geographical location of said area under investigation, said microbial data and a quantity indicative of subsurface hydrocarbon productivity at said location, said at least one geographical location of said area under investigation comprises at least one geographical location at which a quantity indicative of subsurface hydrocarbon productivity at said location refers to absence or presence of hydrocarbon production based on at least one of: assumed hydrocarbon productivity data, known hydrocarbon productivity data, and measured hydrocarbon productivity data obtained from well drilling at said at least one location.

21. The method according to claim 16, wherein said plurality of geographic locations comprises geographic locations of at least one known heterogeneous hydrocarbon play, said at least one heterogeneous hydrocarbon play is selected based on at least one property in common with said area under investigation of a plurality of properties including: type of hydrocarbon source, biogenic and non-biogenic, geology, environment, ecology and climate.

22. The method according to claim 16, wherein steps i)-v) are repeated to provide a refined predictive production map for said plurality of grid positions of said area under investigation, wherein said retrieving in step i) additionally comprises retrieving, by said computer, said microbial data and a measured quantity indicative of subsurface hydrocarbon productivity of at least one grid position having an estimated hydrocarbon productivity quantity qualifying as prospective hydrocarbon productivity quantity in accordance with step iv), and wherein step ii) is performed for all said microbial data and quantities indicative of hydrocarbon productivity retrieved in step i).

23. The method according to claim 16, wherein said estimated hydrocarbon productivity quantities in relation to said corresponding grid positions of said area under investigation are graphically presented at an imaging device, such that estimated hydrocarbon productivity quantities within a predefined range are identically presented, such as by an identical graphically distinguishable marking comprising one of a colouring, hatching and shading.

24. The method according to claim 16, wherein said subsurface heterogeneous hydrocarbon source comprises at least one of a shale gas or shale oil source.

25. The method according to claim 16, wherein said area under investigation is a pre salt area.

26. The method according to claim 16, wherein said microbial data are obtained from DNA analyses of soil samples taken at particular geographical position, and stored in a computer accessible database in association with respective hydrocarbon productivity quantities.

27. The method according to claim 16, wherein said data correlation algorithm is one of a data regression algorithm, a data mining algorithm, a sparse approximation algorithm based on L1-regularization comprising kernel functions and robust parameter estimation by extensive cross validation.

* * * * *